(12) United States Patent
Thiel et al.

(10) Patent No.: US 7,910,744 B2
(45) Date of Patent: Mar. 22, 2011

(54) METHOD FOR THE MANUFACTURE OF SUBSTITUTED PHOSPHANES, AND SUBSTITUTED PHOSPHANES MANUFACTURED ACCORDING TO SAID METHOD

(75) Inventors: Werner Thiel, Kaiserslautern (DE); Yu Sun, Kaiserslautern (DE); Antje Hienzsch, Chemnitz (DE)

(73) Assignee: Zylum Beteiligungsgesellschaft mbH & Co. Patent II KG, Waltersdorf (DE)

( * ) Notice: Subject to any disclaimer, the term of this patent is extended or adjusted under 35 U.S.C. 154(b) by 441 days.

(21) Appl. No.: 11/666,317

(22) PCT Filed: Oct. 17, 2005

(86) PCT No.: PCT/DE2005/001856
§ 371 (c)(1),
(2), (4) Date: Feb. 28, 2008

(87) PCT Pub. No.: WO2006/045272
PCT Pub. Date: May 4, 2006

(65) Prior Publication Data
US 2008/0221335 A1    Sep. 11, 2008

(30) Foreign Application Priority Data

Oct. 27, 2004  (DE) .................. 10 2004 052 725

(51) Int. Cl.
*C07F 9/06* (2006.01)
(52) U.S. Cl. ...................................... 548/112
(58) Field of Classification Search ............. 548/112
See application file for complete search history.

(56) References Cited

U.S. PATENT DOCUMENTS 4,575,499 A * 3/1986 Reifschneider ................ 514/86
6,613,717 B1 * 9/2003 Langemann et al. ......... 504/200

OTHER PUBLICATIONS

PCT International Search Report # PCT/DE2005/001856 date of mailing: Feb. 20, 2006.
Sun Y et al; "Phosphine Ligands Bearing Donar Sties for the Binding of Lewis Acids: Synthesis, Characterization, and Application in Homogeneous Catalysis" Organometallics, ACS, Washington, DC, US, vol. 23, No. 22, Oct. 25, 2004.
Database Beilstein 'Online! Beilstein Institute for Organic Chemistry, Frankfurt-Main, DE; XP002364233 Database accession No. Reaction ID 2888682 abstract & Stanek J. et al: J. Med. Chem., vol. 36, No. 1, 1993, pp. 46-54.
Chapoulaud v G et al: "Synthesis of 4-(2-diphenylphosphino-1-naphthyl)-2-pheny Iquinazoline; a potential P-N chelating ligand for asymmetric catalysis" Tetrahedron letters, Elsevier, Amsterdam, NL, vol. 40, No. 51. Dec. 17, 1999.
Connolly, D. et al.: "Preparation and Resolution of a Modular Class of Axially Chiral Quinazoline-Containing Ligands and Their Application in Asymmetric Rhodium-Catalyzed Olefin Hydroboration" J. Org. Chem., vol. 69, No. 20, Oct. 1, 2004.

* cited by examiner

*Primary Examiner* — Rei-tsang Shiao
(74) *Attorney, Agent, or Firm* — Panitch Schwarze Belisario & Nadel LLP

(57) ABSTRACT

The invention relates to a method for the manufacture of substituted phosphanes and substituted phosphanes manufactured according to the method. Phosphanes, phosphane oxides, sulfides or selenides are used as ligands in coordination compounds. They play a central role in controlling the activity and selectivity of catalysts. The object is achieved by the invention by synthesizing heterocyclic substituents on aromatic groups by introducing acetyl groups. In this manner, previously unknown representatives of the families of phosphanes, phosphane oxides, sulfides and selenides are made accessible.

1 Claim, No Drawings

METHOD FOR THE MANUFACTURE OF SUBSTITUTED PHOSPHANES, AND SUBSTITUTED PHOSPHANES MANUFACTURED ACCORDING TO SAID METHOD

CROSS-REFERENCE TO RELATED APPLICATIONS

This application is a National Stage application which claims the benefit of International Application No. PCT/DE2005/001856, filed May 4, 2006, which claims priority based on DE 10 2004 052 725.3, filed Oct. 27, 2004, each of which is hereby incorporated by reference in full.

BACKGROUND OF THE INVENTION

1. Field of the Invention

The invention relates to a method for the manufacture of substituted phosphanes and to a group of substituted phosphanes manufactured according to the method. Phosphanes are organic compounds of the trivalent phosphorus of the general formula P(R)R')(R"), wherein R, R' and R", respectively, can be the same or different organic substituents. Phosphanes, phosphane oxides, sulfides or selenides are used as ligands in coordination compounds. They play a central role in controlling the activity and selectivity of catalysts.

Due to the commercial interest in these compounds, numerous groups of compounds have already been synthesized. Aromatically and heteroaromatically substituted phosphanes are also already known. They are used in various fields of engineering, e.g. as ligands in homogenous catalytic methods.

2. Description of the Related Art

Since ca. 1970, one has tried to realize increasingly complex substitution patterns in the substituents R, R' and R" to adapt the chemical and physical properties of these compounds to up-to-date problems in technical science. One can mention e.g. chelating phosphanes (several phosphorus centers in one molecule) and chiral phosphanes (for enantioselective catalyses), but also phosphanes carrying heterocycles at the substituents. One example of a heterocyclically substituted phosphane is tri(2-pyridyl)phosphane which is employed as a ligand in various, also technically relevant catalyses.

The easiest way to obtain phosphanes is by reacting compounds of the type $PX_3(X=Cl, Br, I, OR, NR_2)$ with carbon nucleophiles (as a rule organometallic compounds, e.g. LiR, XMgR, $MgR_2$, etc.). This restricts the variation possibilities for the groups R as no organometallic compounds can be obtained from many possible types and e.g. acidic groups are not tolerated. Therefore, a plurality of possible compounds is not yet known at all. Among them are heteroaromatically substituted phosphanes with pyrazole or pyrimidine groups at aromatic compounds that can not be manufactured in the way described above. Correspondingly substituted phosphane oxides, sulfides or selenides are also unknown up to now.

Thus, the object underlying the invention stated in the main claims is to provide a synthesis route for further phosphanes and to provide these phosphanes for controlling the activity and selectivity of catalysts.

This object is achieved by the invention by synthesizing heterocyclic substituents on aromatic groups by the introduction of acetyl groups. In this manner, previously unknown representatives of the compound families phosphanes, phosphane oxides, sulfides and selenides are made accessible. This was surprising as with aromatic phosphanes this synthesis route has neither been known nor expected before.

SUMMARY OF THE INVENTION

The advantages achieved with the invention are in particular that with the methods steps according to the invention, previously unknown phosphanes with one or several aryl(3 (5)-pyrazolyl) or aryl(4-pyrimidinyl) groups can be specifically synthesized with good yields in only a few steps. The synthesis is very variable and permits a wide variation of the matrix as well as of the individual substituents.

The described phosphanes according to the invention are of technical importance in the industrial homogenous catalysis (e.g. as ligands in hydrogenations, C-C-coupling reactions, hydroforming (also in two-phase systems) and many others) as well as in other fields of coordination chemistry (e.g. conductive polymers, material sciences, etc.).

DETAILED DESCRIPTION OF PREFERRED EMBODIMENT

The invention will be represented with reference to the following preferred examples of the syntheses of heterocyclically substituted phosphanes. The manufacture of the individual products will then be illustrated afterwards.

Examples of Synthesized Heterocyclically Substituted Phosphanes

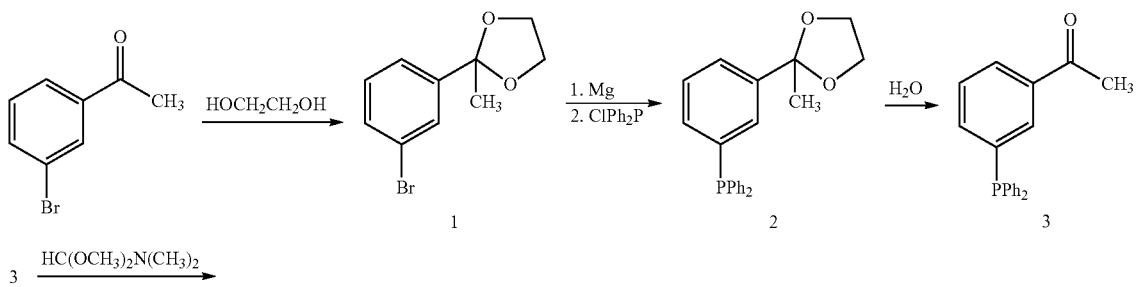

Scheme 1

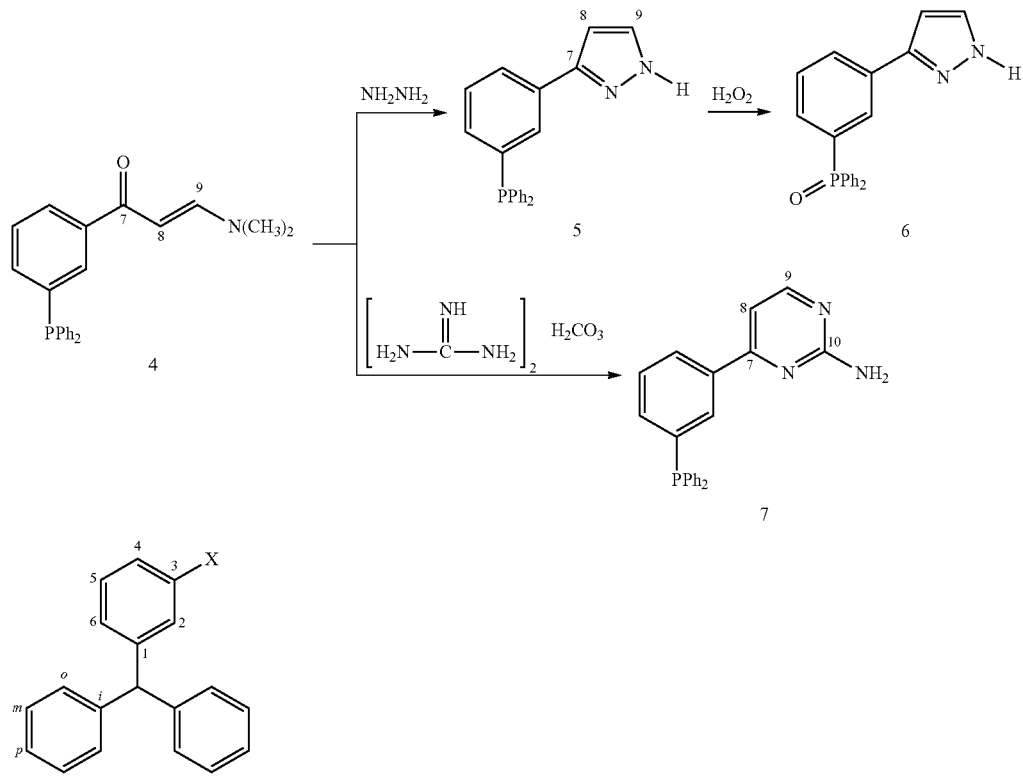

Numbering of the spectra 2-(3-Bromophenyl)-2-methyl-1,3-dioxolane (1). 30.1 g (151 mmol) of (3-bromophenyl)methyl ketone and 13.8 g (222 mmol) of ethylene glycol are dissolved in 120 mL of benzene, mixed with 60 mg of 4-toluenesulphonic acid and boiled under reflux at a water separator (Dean-Stark apparatus) until no more water is separated off. The reaction solution is washed with 50 mL of a 0.5 M $NaHCO_3$ solution, the organic phase is separated off and dried over anhydrous $MgSO_4$. After removal of the benzene in a rotary evaporator, the residue becomes the product with a purity (GC) of 97% in nearly quantitative yield as colorless oily liquid. $C_{10}H_{11}O_2Br$.

[3-(2-Methyl-1,3-dioxolane-2-yl)phenyl]diphenyl phosphane (2). 19.8 g (81.5 mmol) of 2-(3-bromophenyl)-2-methyl-1,3-dioxolane are slowly dropped under cover gas to a suspension of 2.1 g (87.5 mmol) of magnesium in 100 mL of anhydrous THF. After formation of the Grignard reagent, a solution of 16.3 g (73.9 mmol) of chlorodiphenyl phosphane in 50 mL of anhydrous THF is slowly added by dropping at 0° C.

Subsequently, the solution is stirred at 40° C. for another 2 h. After the addition of 50 mL of a degassed concentrated $NH_4Cl$ solution by dropping, the mixture is extracted with toluene/water under cover gas, the organic phase is dried over anhydrous $MgSO_4$ and the solvent is removed in the rotary evaporator. The residue is recrystallized from methanol. The product is obtained in a yield above 80% as colorless crystalline solid (purity: >98%, GC). $C_{22}H_{21}O_2P$.

(3-Acetylphenyl)diphenyl phosphane (3). 25.7 g (73.9 mmol) of [3-(2-methyl-1,3-dioxolane-2-yl)phenyl]diphenylphosphane are dissolved under cover gas in 240 mL of a THF/water mixture (1:1) and mixed with 0.9 g of 4-toluenesulphonic acid. The mixture is boiled under reflux until the original compound is completely reacted. After the addition of 50 mL of a degassed 0.5 M $NaHCO_3$ solution it is washed and after extraction with degassed toluene, the organic phase is separated off and dried over anhydrous $MgSO_4$. The solvent is removed at the rotary evaporator and the residue is purified by column chromatography. The product is obtained in a yield above 70% as colorless oil (purity: >98%, GC). $C_{20}H_{17}OP$.

[3-(3-Dimethylamino-1-oxoprop-2-en-yl)phenyl]diphenyl phosphane (4). A mixture of 9.9 g (32.6 mmol) of (3-acetylphenyl)diphenyl phosphane and 7.7 g (64.7 mmol) of N,N-dimethylformamide dimethylacetal is refluxed under cover gas for 2 h. After removal of the volatiles in high vacuum, the product crystallizes at room temperature. The orange solid is washed with diethyl ether. (Purity: >95%)

$^{31}P\{^1H\}$ NMR). $C_{23}H_{22}ONP$. $^1H$ NMR (250.1 MHz, 25° C., $CDCl_3$): δ 7.87 (t, 2H, $J_{HH}$=8.8 Hz), 7.73 (d, 1H, $^3J_{HH}$=12.3 Hz, 9-H), 7.42-7.26 (m, 12H), 5.56 (d, 1H, 8-H), 2.95 (bd, 6H, $N(CH_3)_2$). $^{13}C\{^1H\}$ NMR (62.9 MHz, 25° C., $CDCl_3$): δ 188.6 (C-7), 154.7 (C-9), 141.0 (d, $^3J_{PC}$=7.2 Hz, C-3), 137.5 (d, $^1J_{PC}$=12.0 Hz, C-1), 137.4 (d, $^1J_{PC}$=10.6 Hz, C-1), 136.4 (d, $^2J_{PC}$=16.3 Hz, C-2), 134.2 (d, $^2J_{PC}$=19.7 Hz, C-p), 133.4 (d, $^2J_{PC}$=23.0 Hz, C-6), 129.2 (s, C-p), 129.0 (d, $^3J_{PC}$=6.7 Hz, C-m), 128.9 (d, $^3J_{PC}$=5.8 Hz, C-5), 128.4 (s, C-4), 92.6 (C-8), 45.5, 37.6 (N(CH$_3$)$_2$). $^{31}$P($^1$H) NMR (101.2 MHz, 25° C., CDCl$_3$); δ −6.36.

[3-(3-Pyrazolyl)phenyl]diphenylphosphane (5). A solution of 1.8 g (5.1 mmol) of [3-(3-dimethylamino-1-oxoprop-2-en-yl)phenyl]diphenyl phosphane and 2.6 g (51 mmol) hydrazine monohydrate in 20 ml of ethanol is heated to boil under cover gas for 3 h. After cooling of the solution to room temperature, the solvent is removed in a vacuum. The remaining colorless oily residue is recrystallized from acetic acid ethyl ester. A colorless solid is obtained (yield: >70%).

C$_{21}$H$_{17}$N$_2$P. $^1$H NMR (250.1 MHz, 25° C., DMSO-d$_6$): δ 12.88 (b, 1H, N—H), 7.81-7.23 (m, 14H), 7.10 (t, 1H, $J_{HH}$=7.3 Hz), 6.60 (d, 1H.

$^3J_{HH}$=2.2 Hz, 8-H). $^{31}$P({$^1$H} NMR (101.2 MHz, 25° C., DMSO-d$_6$); δ −7.55.

[3-(3-Pyrazolyl)phenyl]diphenylphosphane oxide (6). The oxidation of [3-(3-pyrazolyl)-phenyl]diphenylphosphane with 35% H$_2$O$_2$ solution gives the phosphane oxide in a quantitative yield. The compound was characterized by means of X-ray structure analysis.

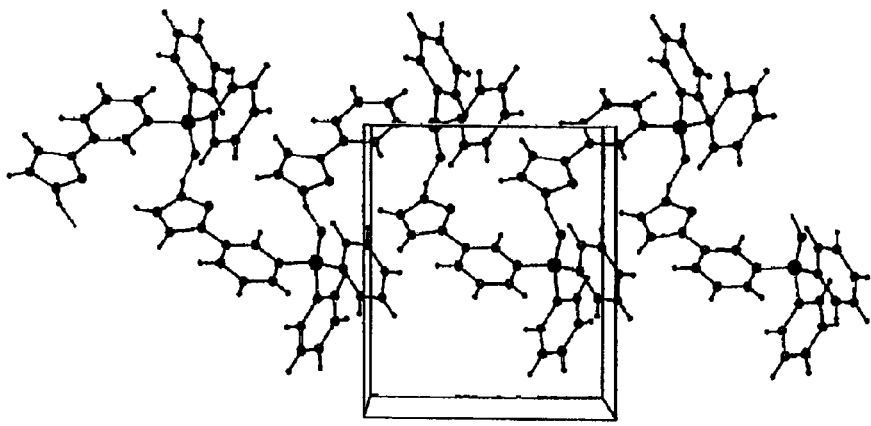

[3-(2-Amino-4-pyrimidinyl)phenyl]diphenylphosphane (7). 2.9 g (7.9 mmol) of [3-(3-dimethylamino-1-oxoprop-2-en-yl)phenyl]diphenylphosphane and 1.5 g (8.5 mmol) of guanidinium carbonate are dissolved under cover gas in 20 mL of ethanol and mixed with a degassed solution of 0.95 g of KOH in 4 mL of H$_2$O. The mixture is heated to 120° C. for 2 h, then neutralized to a pH<4 with diluted HCl and with 25% ammonia solution. A pale yellow sediment is precipitated which is filtered off, washed with diethyl ether and dried (yield: >60%, purity>98%)

$^{31}$P{$^1$H} NMR). C$_{22}$H$_{16}$N$_3$P. $^1$H NMR (250.1 MHz, 25° C. DMSO-d$_6$): δ 8.26 (d, 1H, $^3$J$_{HH}$=5.2 Hz, 9-H), 8.14-8.02 (m, 2H), 7.53-7.17 (m, 12H), 6.99 (d, 1H, 8-H), 6.68 (bs, 2H, NH$_2$). $^{13}$C{$^1$H} NMR (62.9 MHz, 25° C., DMSO-d$_6$): δ 164.7 (C-10), 163.9 (C-7), 160.1 (C-9), 138.2 (d, $^2$J$_{PC}$=18.2 Hz, C-6), 138.2 (d, $^3$J$_{PC}$=2.8 Hz, C-3), 137.2 (d, $^1$J$_{PC}$=11.2 Hz, C-1), 135.6 (d, $^1$J$_{PC}$=11.7 Hz, C-1), 134.2 (d, $^2$J$_{PC}$=19.6 Hz, C-o), 132.7 (d, $^2$J$_{PC}$=28.7 Hz, C-2), 130.1 (d, $^3$J$_{PC}$=4.3 Hz, C-5), 130.0 (s, C-p), 129.7 (d, $^3$J$_{PC}$=6.8 Hz, C-m), 128.3 (s, C-4), 106.7 (C-8). $^{31}$P{$^1$H} NMR (101.2 MHz, 25° C., DMSO-d$_6$): δ −7.60.

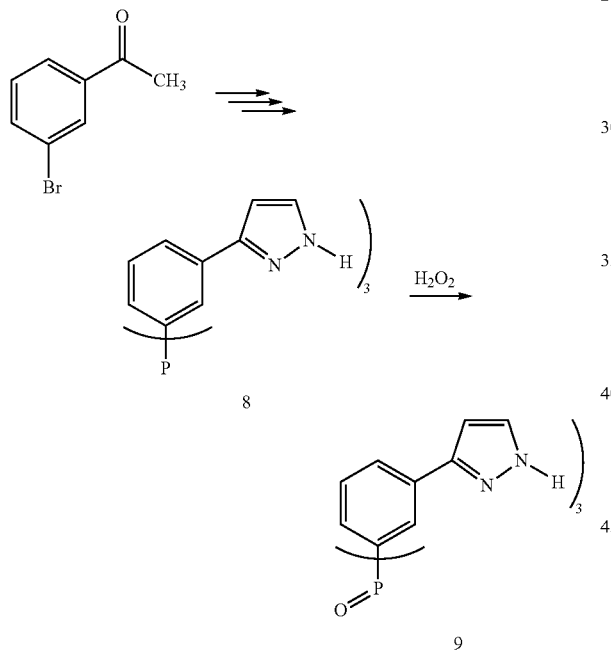

Schema 2

8

9

Tri[3-(3-pyrazolyl)phenyl]phosphane (8) and Tri[3-(3-pyrazolyl)phenyl]phosphane oxide (9) are synthesized analogously to scheme 1. In this case, the Grignard reagent of 1 is reacted with phosphorus trichloride instead of chlorodiphenylphosphane. As an intermediate, tri[3-(3-dimethylamino-1-oxoprop-2-en-yl)phenyl]phosphane is obtained.

Tri [3-(3-dimethylamino-1-oxoprop-2-en-yl)phenyl] phosphane.

$^1$H NMR (400.1 MHz, 25° C., CDCl$_3$): δ 7.91, 7.85 (2 d, 6H, $^3$J$_{HH}$=7.5 Hz, $^3$J$_{HH}$=8.5 Hz, 4-H, 6H), 7.79 (d, 3H, $^3$J$_{HH}$=12.2 Hz, =CHN(CH$_3$)$_2$), 7.44-7.35 (m, 6H, 2-H, 5-H), 5.55 (d, 3H, COCH=), 3.12, 2.85 (2 s, 18H, N(CH$_3$)$_2$). $^{13}$C{$^1$H} NMR (100.6 MHz, 25° C. CDCl$_3$): δ 188.2 (C=O), 155.0 (=CHN(CH$_3$)$_2$), 141.0 (d, $^3$J$_{PC}$=7.4 Hz, C-3), 137.1 (d, $^1$J$_{PC}$=12.0 Hz, C-1), 136.4 (d, $^2$J$_{PC}$=17.6 Hz, C-6), 133.3 (d, $^2$J$_{PC}$=23.1 Hz, C-2), 129.0 (d, $^3$J$_{PC}$=6.5 Hz, C-5), 128.6 (s, C-4), 92.7 (COCH=), 45.4, 37.8 (N(CH$_3$)$_2$). $^{31}$P{$^1$H} NMR (162.0 MHz, 25° C., CDCl$_3$): δ −3.89.

Tri[3-(3-pyrazolyl)phenyl]phosphane (8).
$^1$H NMR (400.1 MHz, 25° C., DMSO-d$_6$); δ 12.94 (br, 3H, N—H), 7.88-7.80 (m, 6H, ar H), 7.71 (d, 3H, $^3$J$_{HH}$=2.4 Hz, 5$_{pz}$-H), 7.51-7.44 (m, 3H, ar H), 7.23-7.18 (m, 3H, ar H), 6.65 (d, 3H, 4$_{pz}$-H). C{$^1$H} NMR (100.6 MHz, 25° C., DMSO-d$_6$): δ 148.7 (C-3$_{pz}$), 138.0 (d, $^1$J$_{PC}$=12.0 Hz, C-1), 134.2 (d, $^3$J$_{PC}$=6.5 Hz, C-3), 133.0 (d, $^2$J$_{PC}$=16.6 Hz, C-6), 130.9 (d, $^2$J$_{PC}$=24.0 Hz, C-2), 130.0 (d, $^3$J$_{PC}$=6.5 Hz, C-5), 126.8 (s, C-4), 102.8 (C-4$_{pz}$), C-5$_{pz}$ not observed. $^{31}$P{$^1$H} NMR (162.0 MHz, 25° C., DMSO-d$_6$): δ −4.44.

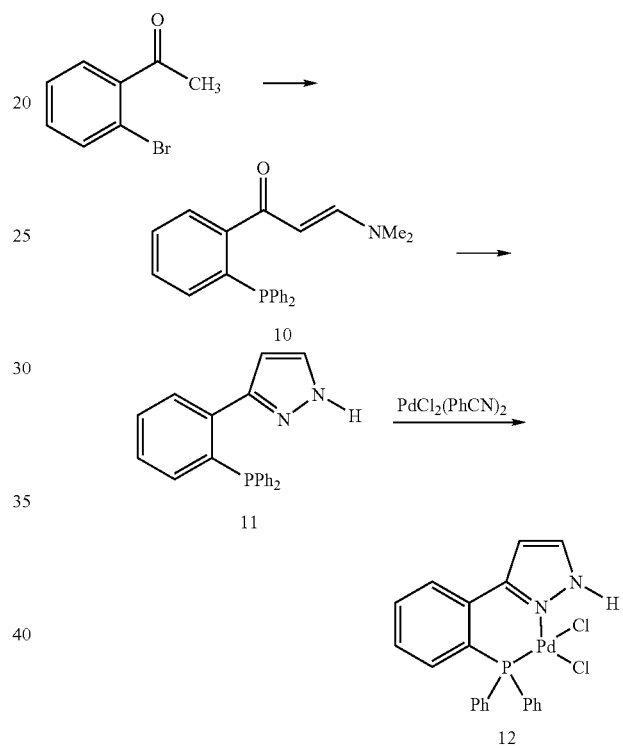

Schema 3

10

11

12

[2-(3-Dimethylamino-1-oxoprop-2-en-yl)phenyl]diphenylphosphane (10). 10 is synthesized according to the same reaction route as the isomeric compound 4. Here, one starts from (2-bromophenyl)methyl ketone instead of (3-bromophenyl)methyl ketone. Yield: 85%.

$^1$H NMR (400.1 MHz, 25° C., CDCl$_3$): δ 7.66-7.63 (m, 1H, 3-H), 7.38 (td, $^3$J$_{HH}$=7.5 Hz, $^4$J$_{HH}$=1.2 Hz, 1H, 5-H or 4-H), 7.31-7.27 (m, 12H, ar H, =CHN(CH$_3$)$_2$), 7.07-7.04 (m, 1H, 6-H), 5.42 (d, $^3$J$_{HH}$=12.5 Hz, 1H, COCH=), 2.96, 2.71 (2 s, 6H, N(CH$_3$)$_2$). $^{13}$C{$^1$H} NMR (100.6 MHz, 25° C., CDCl$_3$): δ 192.0 (C=O), 155.0 (=CHN(CH$_3$)$_2$), 148.1 (d, $^2$J$_{PC}$=27.0 Hz, C-2), 139.3 (d, $^1$J$_{PC}$=12.1 Hz, C-1), 136.5 (d, $^2$J$_{PC}$=19.5 Hz, C-6), 135.0 (s, C-1), 134.2 (d, $^2$J$_{PC}$=19.8 Hz, C-o), 129.6 (s, C-5), 128.7 (s, C-4), 128.6 (d, $^3$J$_{PC}$=6.7 Hz, C-m), 128.5 (s, C-p), 127.9 (d, $^3$J$_{PC}$=5.4 Hz, C-3), 97.1 (COCH=), 45.2, 37.3 (N(CH$_3$)$_2$). $^{31}$P{$^1$H} NMR (162.0 MHz, 25° C., CDCl$_3$): δ −8.76.

[2-(3-Pyrazolyl)phenyl]diphenylphosphane (11). 11 is synthesized according to the same reaction route as the isomeric compound 5. Here, one starts from 10 (scheme 3). Yield: 96%.

¹H NMR (400.1 MHz, 25° C., DMSO-d$_6$): δ 12.94 (br, 1H, N—H), 7.66-7.62 (m, 2H, 3-H, 5$_{pz}$-H), 7.44 (t, $^3J_{HH}$=7.4 Hz, 1H, 4-H), 7.36-7.34 (m, 6H, m, p-H), 7.27 (t, 1H, 5-H), 7.19-7.15 (m, 4H, o-H), 6.92-6.90 (m, 1H, 6-H), 6.30 (br, 1H, 4$_{pz}$-H). $^{13}$C{¹H} NMR (100.6 MHz, 25° C., DMSO-d$_6$): δ 150.8 (C-3$_{pz}$), 140.2 (C-5$_{pz}$), 138.8 (br, C-1), 135.9 (d, $^2J_{PC}$=18.8 Hz, C-2), 134.8 (s, C-1), 134.2 (d, $^2J_{PC}$=19.9 Hz, C-o), 132.1 (d, $^2J_{PC}$=9.2 Hz, C-6), 130.5 (d, $^3J_{PC}$=4.8 Hz, C-5), 129.7 (s, C-4), 129.4 (d, $^3J_{PC}$=6.5 Hz, C-m), 129.4 (s, C-p), 128.5 (s, C-3), 106.5 (C-4$_{pz}$). $^{31}$P{¹H} NMR (162.0 MHz, 25° C., DMSO-d$_6$): δ −10.46.

The palladium dichloro complex 12 can be obtained from 11 (molecular structure from X-ray structure analysis below). Yield: quantitative.

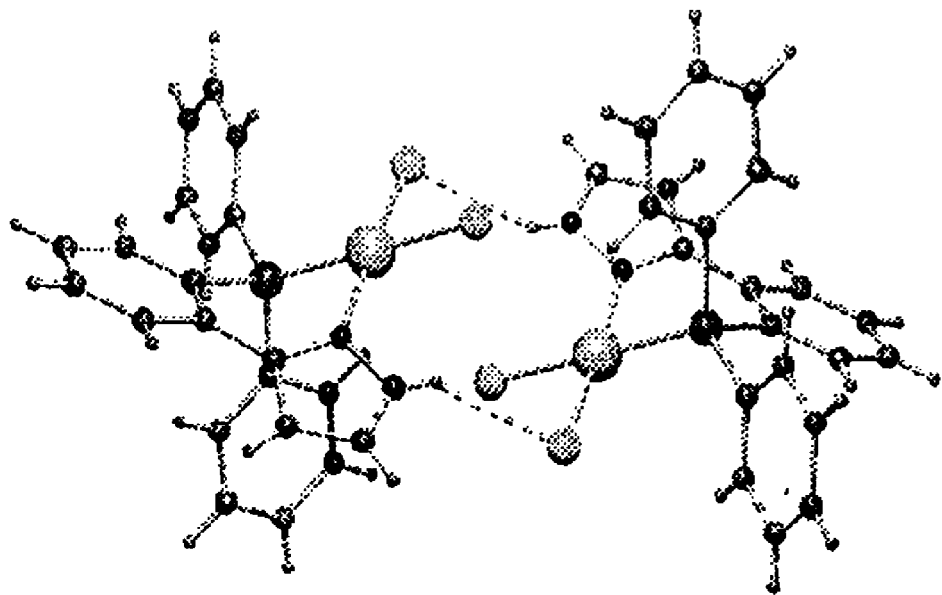

Dichloro{[2-(3-pyrazolyl)phenyl]diphenylphosphane}palladium(II) (12).

$^1$H NMR (400.1 MHz, 25° C., DMSC-d$_6$): δ 13.23 (br, 1H, N—H), 8.15-8.12 (m, 1H, 3-H), 7.99 (br, 1H, 5$_{pz}$-H), 7.82 (t, $^3J_{HH}$=7.4 Hz, 1H, 4-H), 7.65-7.45 (m, 1H, ar H), 7.13 (br, 1H, 4$_{pz}$-H), 6.99-6.95 (m, 1H, 6-H). $^{31}$P{$^1$H} NMR (162.0 MHz, 25° C., DMSO-d$_6$): δ 26.96.

Schema 4

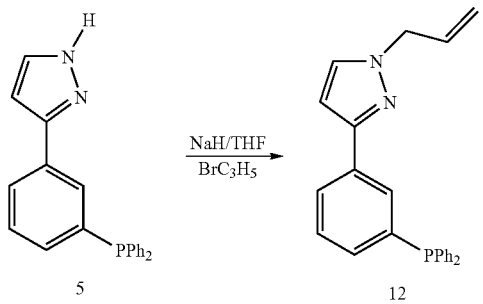

[3-(1-Allylpyrazol-3-yl)phenyl]diphenylphosphane (12). 25 mmol of 5 are dissolved in 50 ml of THF and mixed with 25 mmol of NaH. After the termination of the evolution of hydrogen, 25 mmol of allyl bromide are added and the mixture is refluxed for 4 h. After cooling to room temperature, it is filtered off from the NaBr precipitation and the solvent is removed in a vacuum. A colorless oil remains. Yield: 98%. $^1$H NMR (400.1 MHz, 25° C., DMSO-d$_6$): δ 7.80-7.25 (m, 14H, ar H, 5$_{pz}$-H), 7.06 (t, 1H, $^3J_{HH}$=6.6 Hz, 5-H), 6.63 (d, 1H, $^3J_{HH}$=2.4 Hz, 4$_{pz}$-H), 6.07-5.96 (m, 1H, —CH=CH$_2$), 5.20-5.11 (m, 2H, —CH=CH$_2$), 4.75 (d, 2H, $^3J_{HH}$=5.7 Hz, —CH$_2$CH=). $^{13}$C{$^1$H} NMR (100.6 MHz, 25° C., DMSO-d$_6$): δ 150.5 (C-3$_{pz}$), 139.4 (C-5$_{pz}$), 137.6 (d, $^1J_{PC}$=12.0 Hz, C-1), 134.7 (—CH=CH$_2$), 134.1 (d, $^2J_{PC}$=19.4 Hz, C-o), 132.9 (d, $^3J_{PC}$=2.8 Hz, C-3), 132.8 (d, $^2J_{PC}$=14.8 Hz, C-6), 132.4 (d, $^1J_{PC}$=9.2 Hz, C-1), 130.9 (d, $^2J_{PC}$=25.0 Hz, C-2), 130.0 (d, $^3J_{PC}$=4.6 Hz, C-5), 129.8 (s, C-p), 129.6 (d, $^3J_{PC}$=6.5 Hz, C-m), 126.7 (s, C-4), 118.7 (—CH=CH$_2$), 103.6 (C-4$_{pz}$) 54.7 (—CH$_2$CH=). $^{31}$P{$^1$H} NMR (162.0 MHz, 25° C., DMSO-d$_6$): δ 4.90.

Schema 5

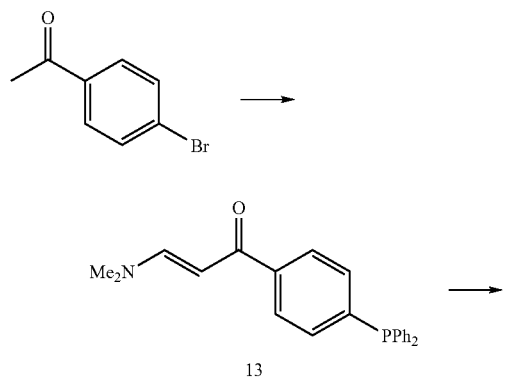

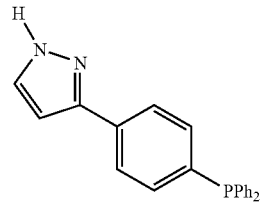

[4-(3-Dimethylamino-1-oxoprop-2-en-yl)phenyl]diphenylphosphane (13). 13 is synthesized according to the same reaction route as the isomeric compounds 4 and 10. Here, one starts from (4-bromophenyl)methyl ketone. Yield: 97%.

$^1$H NMR (400.1 MHz, 25° C., CDCl$_3$): δ 7.75-7.10 (m, 15H, ar H, =CHN(CH$_3$)$_2$), 5.45 (d, $^3J_{PC}$=12.7 Hz, 1H, COCH=), 2.97, 2.73 (2 s, 6H, N(CH$_3$)$_2$). $^{31}$P{$^1$H} NMR (162.0 MHz, 25° C. CDCl$_3$): δ −8.25.

[4-(3-Pyrazolyl)phenyl]diphenylphosphane (14). This compound is synthesized according to the same reaction route as the isomeric compounds 5 and 10. Here, one starts from 13.

$^1$H NMR (400.1 MHz, 25° C., DMSO-d$_6$): δ 13.02 (br, 1H, N—H), 7.70-7.12 (m, 15H, ar H, 5$_{pz}$-H), 6.33 (br, 1H, 4$_{pz}$-H). $^{31}$P{$^1$H} NMR (162.0 MHz, 25° C., DMSO-d$_6$): δ −10.02.

Schema 6

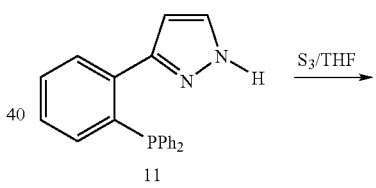

[2-(3-Pyrazolyl)phenyl]diphenylphosphane sulfide (15). The reaction of 11 with elemental sulfur in a toluene solution gives 15 in a quantitative yield.

$^1$H NMR (250.1 MHz, 25° C., DMSO-d$_6$): δ 13.00 (b, 1H, N—H), 7.87-7.18 (m, 15H, ar-H, pz-H), 6.62 (d, 1H, $^3J_{HH}$=2.2 Hz, pz-H). $^{31}$P{$^1$H} NMR (101.2 MHz, 25° C., DMSO-d$_6$): δ 52.3.

Schema 7

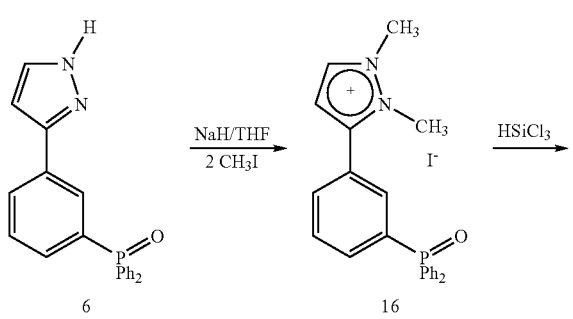

[3-(1,2-Dimethyl-3-pyrazolium)phenyl]diphenylphosphane oxide (16). 25 mmol of 6 are dissolved in 50 ml of THF and mixed with 25 mmol of NaH. After the termination of the evolution of hydrogen, 50 mmol of methyl iodide are added and the mixture is refluxed for 10 h. After cooling to room temperature, the solvent is removed in a vacuum, the residue is washed with water and acetic ester and dried in a vacuum. A colorless solid remains. Yield: 80%.

$^1$H NMR (400.1 MHz, 25° C., DMSO-d$_6$): δ 7.83-7.33 (m, 14H, ar H, 5$_{pz}$-H), 7.04 (t, 1H, $^3J_{HH}$=6.6 Hz, 5-H), 6.95 (d, 1H, $^3J_{HH}$=2.0 Hz, 4$_{pz}$-H), 3.13, 3.04 (2×s, 6H, 2×CH$_3$). $^{31}$P{$^1$H} NMR (101.2 MHz, 25° C., DMSO-d$_6$): δ 25.4.

[3-(1,2-Dimethyl-3-pyrazolium)phenyl]diphenylphosphane (17). 20 mmol of 16 are dissolved in 50 ml of toluene, mixed with a four-fold excess of HSiCl$_3$ and heated to 100° C. for 4 h. After cooling to room temperature, it is carefully hydrolyzed with saturated sodium hydrogencarbonate solution, the organic phase is separated off and dried over MgSO$_4$. After the removal of the solvent, a colorless solid remains. Yield: 55%.

$^1$H NMR (400.1 MHz, 25° C., DMSO-d$_6$): δ 7.75-7.31 (m, 14H, ar H, 5$_{pz}$-H), 7.06 (t, 1H, $^3J_{HH}$=6.6 Hz, 5-H), 6.94 (d, 1H, $^3J_{HH}$=2.0 Hz, 4$_{pz}$-H), 3.11, 3.07 (2×s, 6H, 2×CH$_3$). $^{31}$P{$^1$H} NMR (101.2 MHz, 25° C., DMSO-d$_6$): δ 25.4.

$^3J_{HH}$=6.6 Hz, 5-H), 6.94 (d, 1H, $^3J_{HH}$=2.0 Hz, 4$_{pz}$-H), 3.11, 3.07 (2×s, 6H, 2×CH$_{31}$). $^{31}$P{$^1$H} NMR (101.2 MHz, 25° C., DMSO-d$_6$): δ 25.4.

[2-(4,4,4-Trifluoromethyl-1,3-dioxapropanyl)phenyl]diphenylphosphane (18). 40 mmol of o-(acetylphenyl)diphenylphosphane are added to a suspension of 80 mmol of NaOMe in 200 ml of THF. To the yellow-colored solution, 40 mmol of trifluoroacetic acid ethyl ester are dropped, whereupon the color changes to orange-red. The mixture is refluxed for 4 h, then the solvent is removed in a vacuum and the residue is received in 100 ml of a 1:1 water/ChCl$_3$ mixture. The pH value of the aqueous solution is adjusted to 4 with acetic acid. After a threefold extraction of the aqueous phase with 50 ml of CHCl$_3$, the organic phases are combined and dried over MgSO$_4$. After the removal of the solvent, a yellowish oil remains from which a colorless solid was obtained by crystallization from acetic acid ethyl ester. Yield: 63%.

$^1$H NMR (400.1 MHz, 25° C., CDCl$_3$): δ 7.70-7.31 (m, 14H, ar-H), 4.25 (s, 2H, CH$_2$). $^{13}$C{$^1$H} NMR (100.6 MHz, 25° C., CDCl$_3$): δ 194.5, 198.2 (2×C=O), 148.4, 139.1, 136.0, 134.7, 134.2, 129.8, 128.6, 128.5, 128.1, 127.5 (all C-ar), 121.3 (q, $^1J_{CF}$=265 Hz, CF$_3$). 65.4 (CH$_2$). $^{31}$P{$^1$H} NMR (162.0 MHz, 25° C., CDCl$_3$): δ −6.55.

[2-(5-Trifluoromethylpyrazol-3-yl)phenyl]diphenylphosphane (19). 19 is obtained in a yield of 96% by condensation of 18 with hydrazine in ethanol in analogy to the pyrazoles 5, 10 and 14.

$^1$H NMR (400.1 MHz, 25° C., DMSO-d$_6$): δ 13.87 (br, 1H, N—H), 7.66-6.90 (m, 15H, ar-H, pz-H). $^{13}$C{$^1$H} NMR (100.6 MHz, 25° C., DMSO-d$_6$): δ 150.8 (C-3$_{pz}$), 138.9 136.5, 135.1, 134.2, 132.2, 130.5, 129.8, 129.4, 129.4, 125.4, (q, $^1J_{CF}$=271 Hz, CF$_3$). 113.3 (C-4$_{pz}$), 92.6 (q, $^2J_{CF}$=31 Hz, C-5$_{pz}$). $^{31}$P{$^1$H} NMR (162.0 MHz, 25° C., DMSO-d$_6$): δ −9.22.

Schema 9

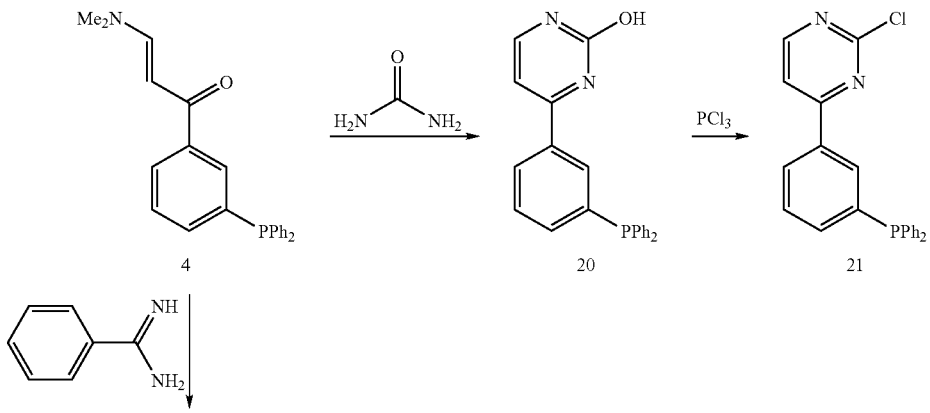

-continued

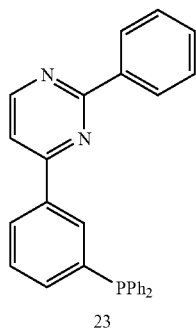

23

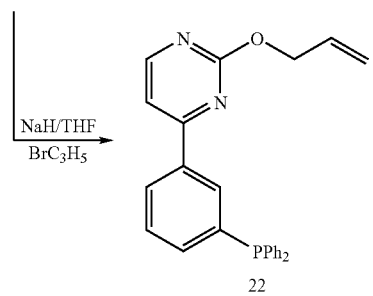

22

[3-(2-Hydroxy-4-pyrimidinyl)phenyl]diphenylphosphane (20). 10 mmol of 4 are dissolved in 100 ml of aqueous ethanol and mixed with 25 mmol of urea. It is refluxed for 7 h, the solvent is removed and the colorless solid is washed with water. Recrystallization from chloroform gives 20 in a yield above 90%. ESI MS, m/z (%): 366.3703 (100) [M+H]$^+$. $^{31}$P{$^1$H} NMR (101.2 MHz, 25° C., DMSO-d$_6$): 5-7.45.

[3-(2-Chloro-4-pyrimidinyl)phenyl]diphenylphosphane (21). 5 mmol of 20 are dissolved in 50 ml of CHCl$_3$ and mixed with 10 mmol of PCl$_3$. It is refluxed for 30 min, the volatiles are removed in a vacuum and the colorless solid is washed with water. Recrystallization from chloroform gives 21 in a yield above 90%. ESI MS, m/z (%): 375.8154 (100) [M+H]$^+$. $^{31}$P{$^1$H} NMR (101.2 MHz, 25° C., DMSO-d$_6$): δ −7.40.

[3-(2-Chloro-4-pyrimidinyl)phenyl]diphenylphosphane (22). 5 mmol of 20 are dissolved in 50 ml of THF and mixed with 5 mmol of NaH. After the termination of the evolution of hydrogen, 5 mmol of allyl bromide are added and the mixture is refluxed for 3 h. After cooling to room temperature, it is filtered off from the NaBr precipitation and the solvent is removed in a vacuum. A colorless solid remains. Yield: quantitative. ESI MS, m/z (%): 397.4345 (100) [M+H]$^+$. $^{31}$P{$^1$H} NMR (101.2 MHz, 25° C., DMSO-d$_6$): 6-7.55.

[3-(2-Phenyl-4-pyrimidinyl)phenyl]diphenylphosphane (23). 10 mmol of 4 are dissolved in 100 ml of ethanol and mixed with 10 mmol of benzamidine. The mixture is refluxed for 90 min, subsequently the solvent is removed. Recrystallization from acetic acid ethyl ester gives a colorless solid. Yield: 79%. ESI MS, m/z (%): 417.4674 (100) [M+H]$^+$. $^{31}$P{$^1$H} NMR (101.2 MHz, 25° C., DMSO-d$_6$): δ −7.37.

The following illustrations show a selection of reaction schemes for further compounds according to the invention by way of example, which is by no means complete:

Synthesis of the Starting Compounds with the Ortho Substituted Benzene Derivative as an Example

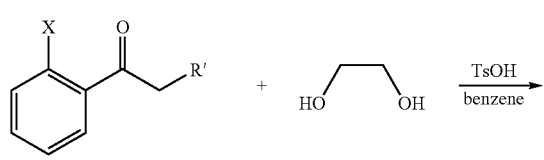

R' = H, alkyl group, aryl group
X = Cl, Br, I

-continued

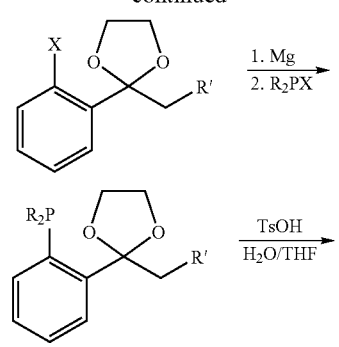

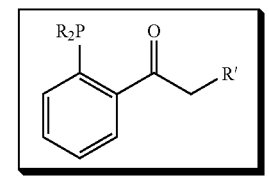

R = alkyl group, aryl group
X = Cl, Br, I, NR$_2$, OR
for further variants, see next page
some representatives of these
are known, are not in the claim possible product variants (examples):
meta or para instead of ortho substitution        higher substituted phenyl ring

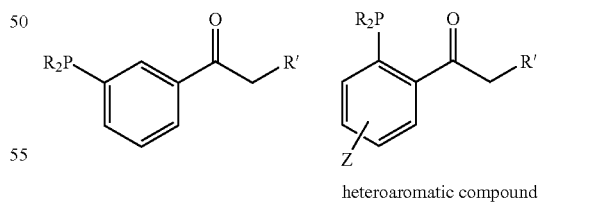

heteroaromatic compound

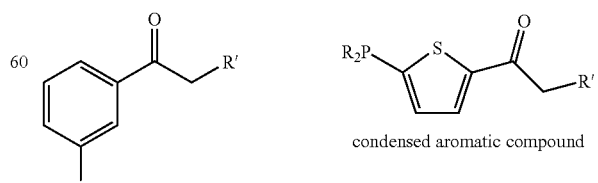

condensed aromatic compound

21
-continued possible product variants (examples):
meta or para instead of ortho substitution    higher substituted phenyl ring

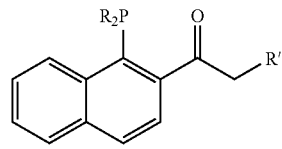

Synthesis of the Starting Compounds with the Ortho Substituted Benzene Derivative as an Example Further Product Variants by Variation of the Phosphorus Reagent

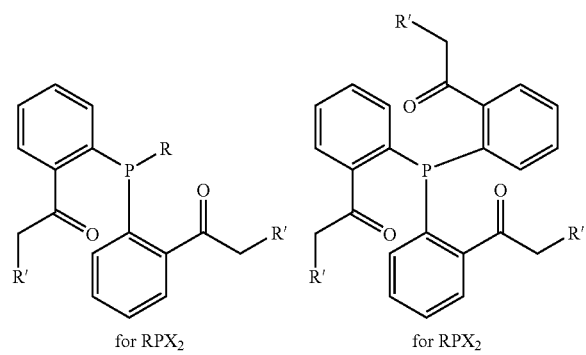

for RPX$_2$    for RPX$_2$

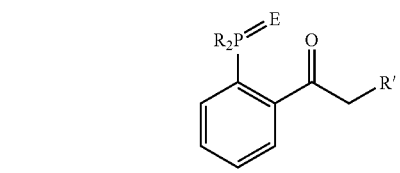

for R$_2$P(E)X
E = O, S, Se

Arylphosphanes with 3-aminopropen-1-on substituents or 1,3-dioxapropyl Substituents, Respectively

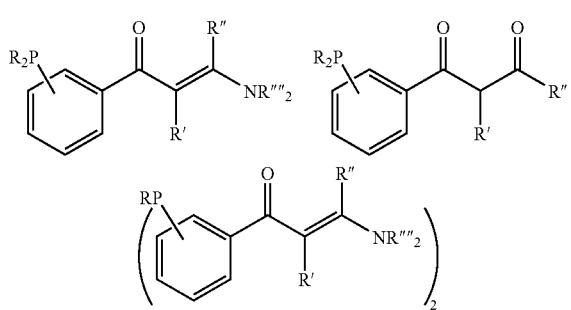

22
-continued

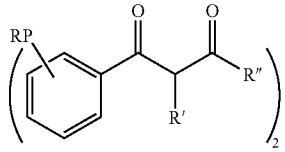

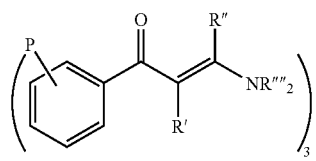

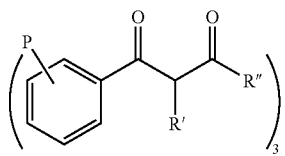

R″ = H, alkyl group, aryl group
R‴ = alkyl group
R″″ = alkyl group, also cyclic ——NR″″$_2$ group Synthesis of the arylphosphanes with 3-aminopropen-1-on substituents or with 1,3-dioxapropyl substituents, respectively

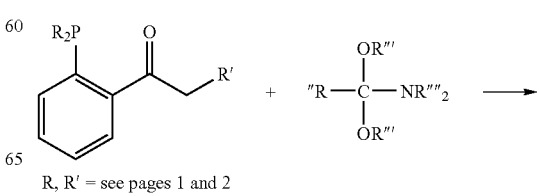

R, R′ = see pages 1 and 2

-continued

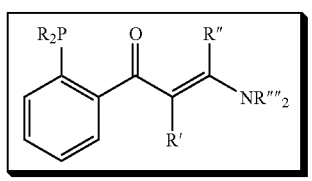

is in the claim

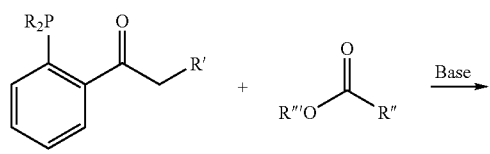

R, R' = see pages 1 and 2

-continued

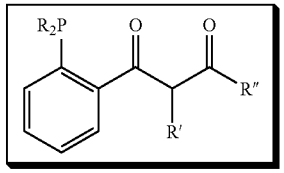

is in the claim

R'' = H, alkyl group, aryl group
R''' = alkyl group
R'''' = alkyl group, also cyclic —NR''''$_2$ group Arylphosphanes with 3-aminopropen-1-on substituents or with 1,3-dioxapropyl Substituents, Respectively Exemplary Synthesis Possibilities

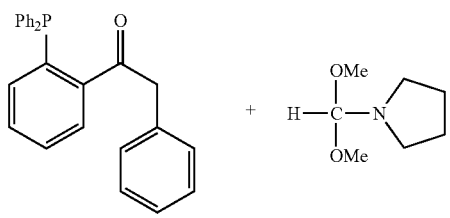

from o-chlorobenzonitrile and benzylmagnesium bromide

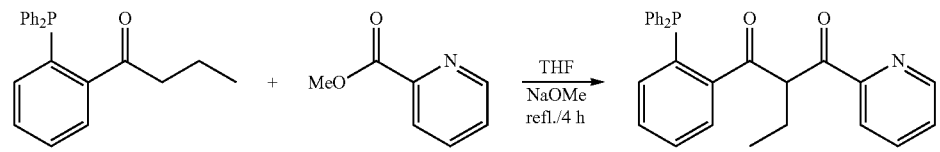

from o-chlorobenzonitril and propylmagnesium bromide

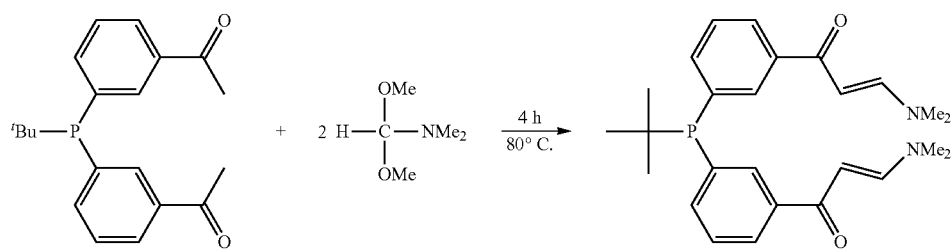

from $^t$BuPCl$_2$ and the corresp. o-substit. Grignard reagent

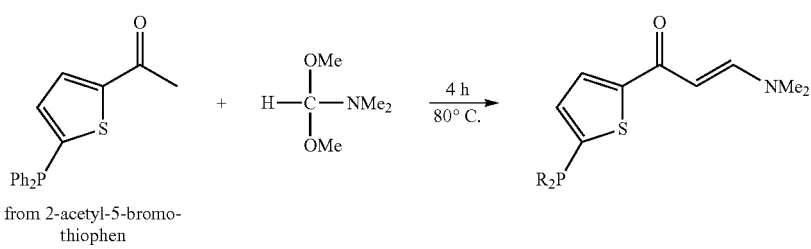

from 2-acetyl-5-bromo-thiophen

-continued
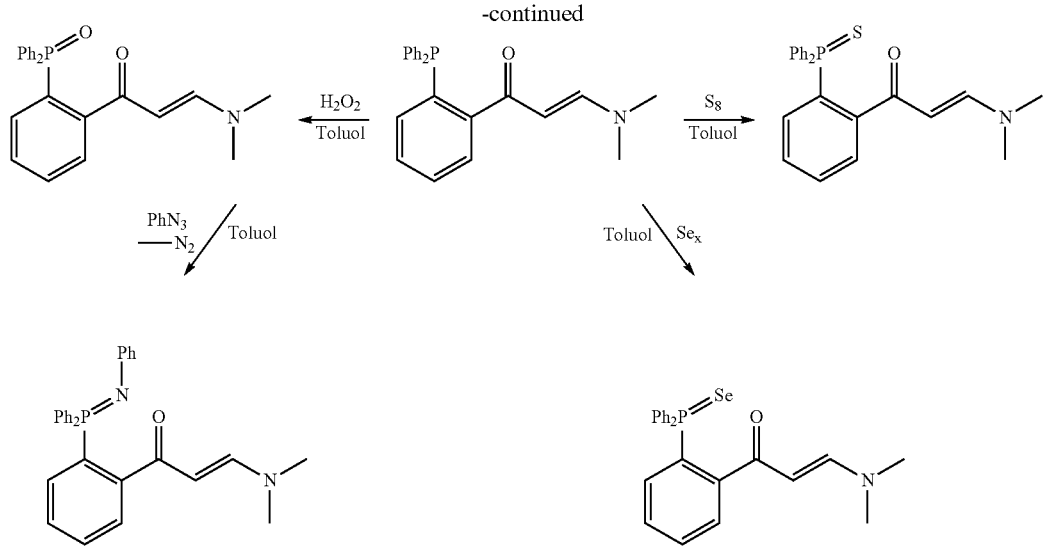
Arylphosphanes with 3-aminopropen-1-on substituents or with 1,3-dioxapropyl Substituents Exemplary Synthesis Possibilities for Binaphthyl Compound
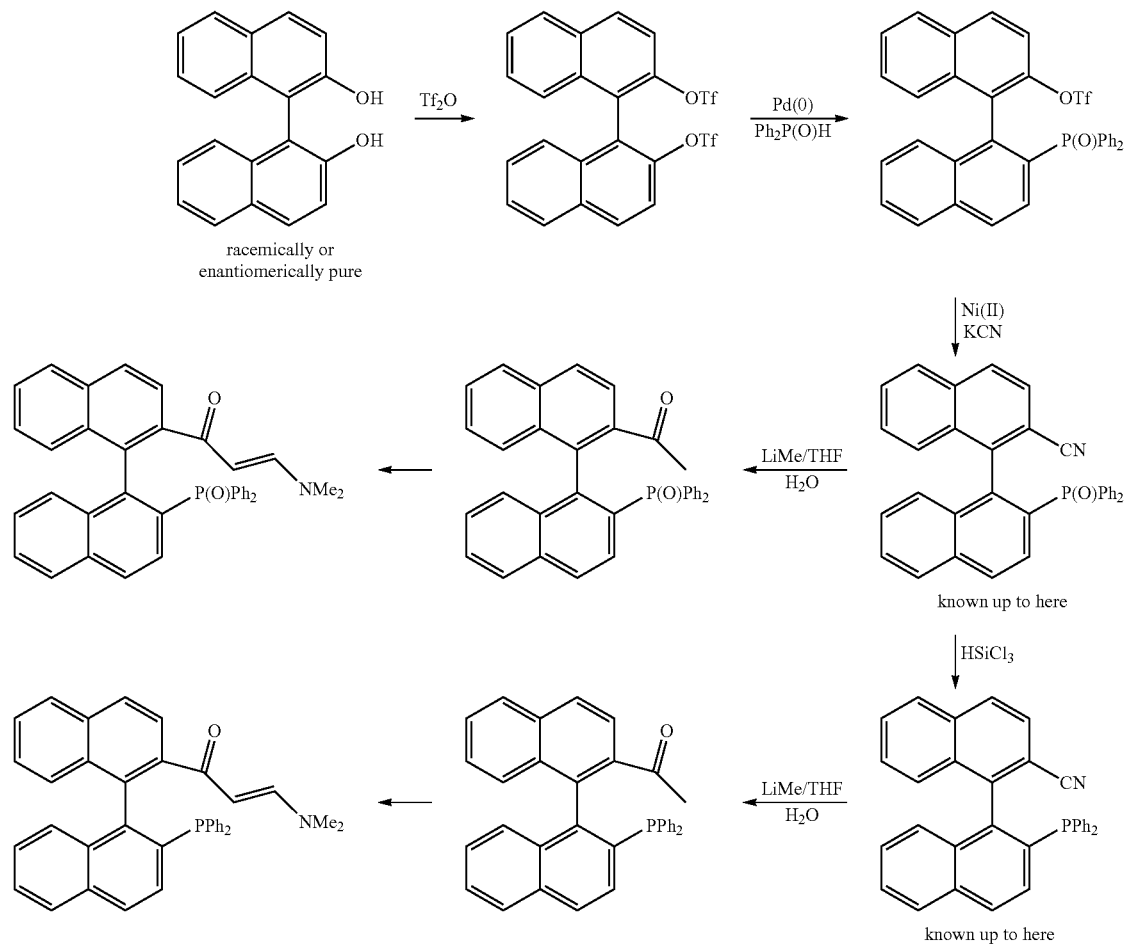

Arylphosphanes with Prazolyl Substituents
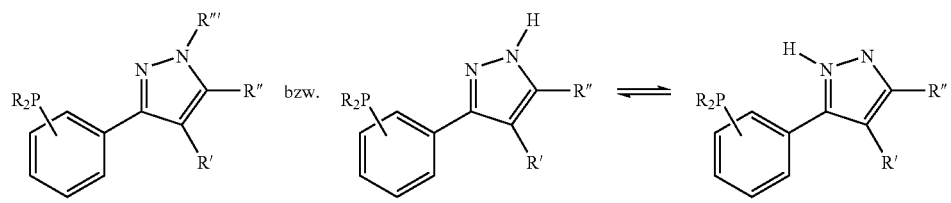
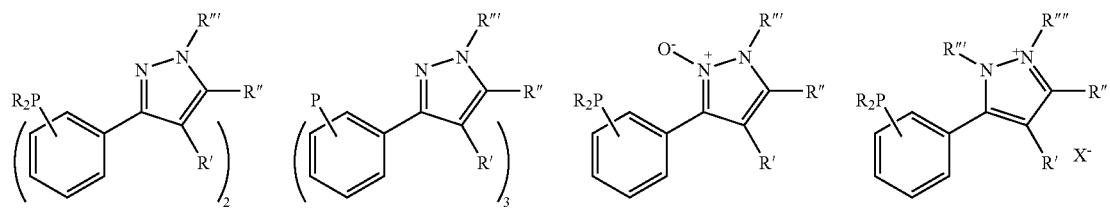
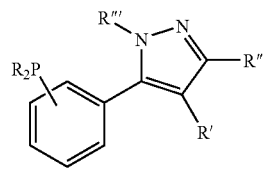
Synthesis of the Arylphosphanes with Prazolyl Substituents
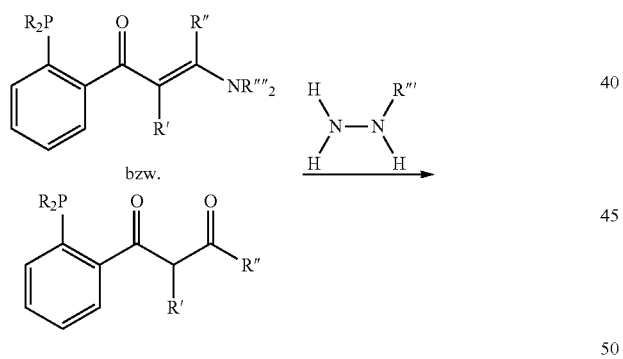
are both in the claim
-continued
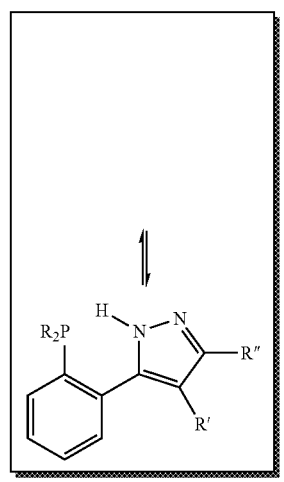
R''' = H, alkyl group, aryl group
Possible Product Variants (Examples):
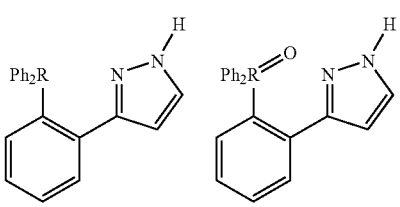

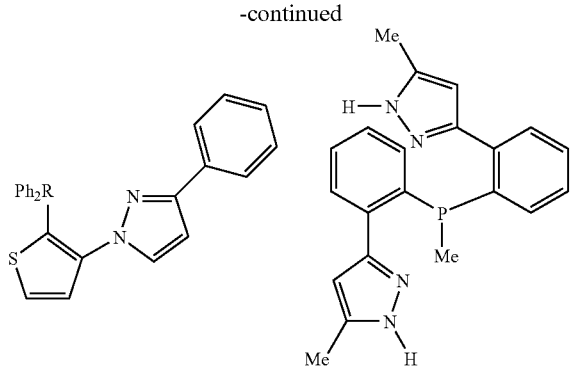
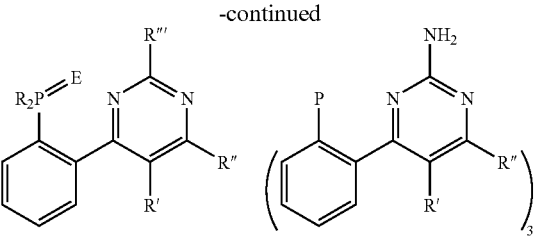

Arylphosphanes with Prazolyl Substituents
Exemplary Synthesis Possibilities

The ring closure with hydrazine is in all cases effected starting from the 3-aminopropenones or the 1,3-diketones by refluxing in ethanolic solution for several hours.

Further derivatization:

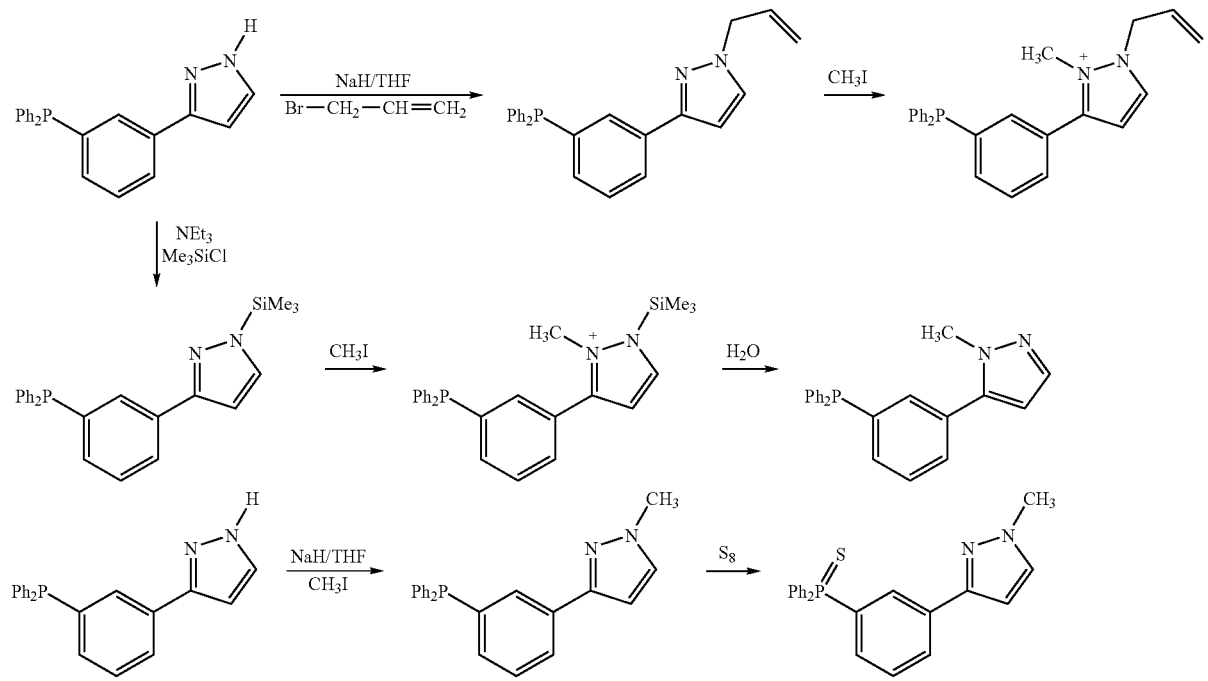

Arylphosphanes with Pyrimidinyl Substituents

Synthesis of the Arylphosphanes with Pyrimidinyl Substituents

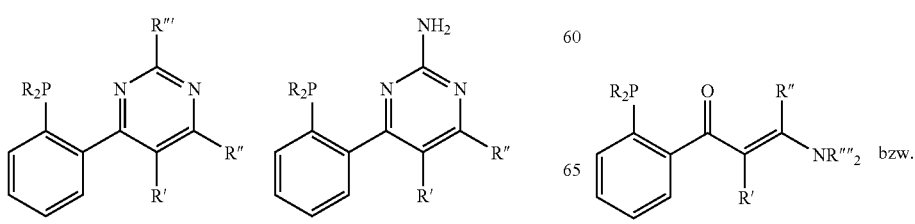

bzw.

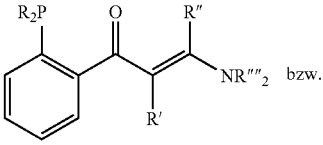

-continued
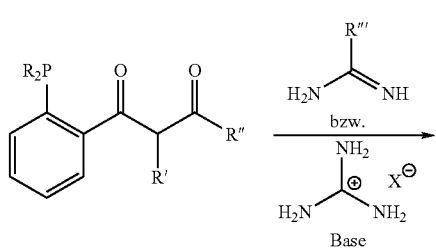
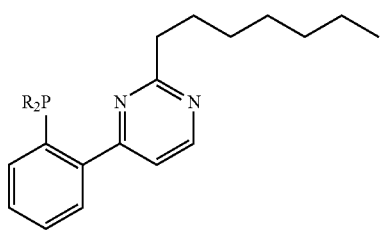
Possible Product Variants (Examples):
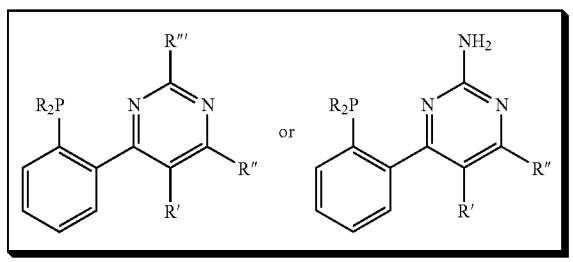
are both in the claim
R''' = H, alkyl group, aryl group
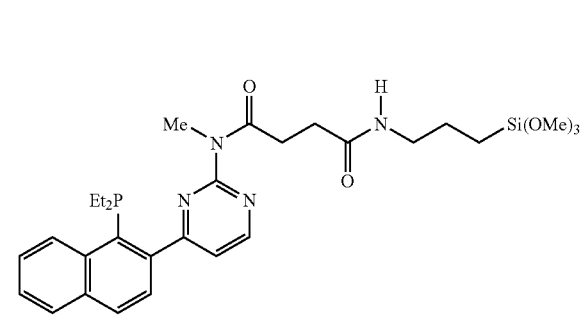
Arylphosphanes with Pyrimidinyl Substituents
Exemplary Synthesis Possibilities
The ring closure is effected starting from the 3-aminopropenones or the 1,3-diketones and is illustrated here with the o-substituted diphenylphosphino derivative.
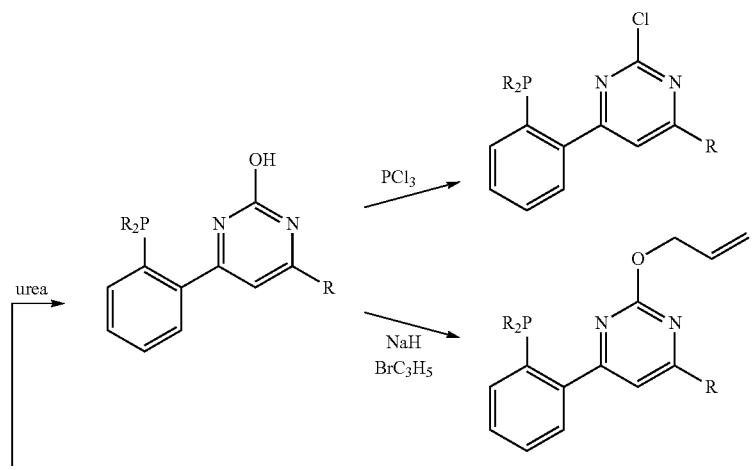

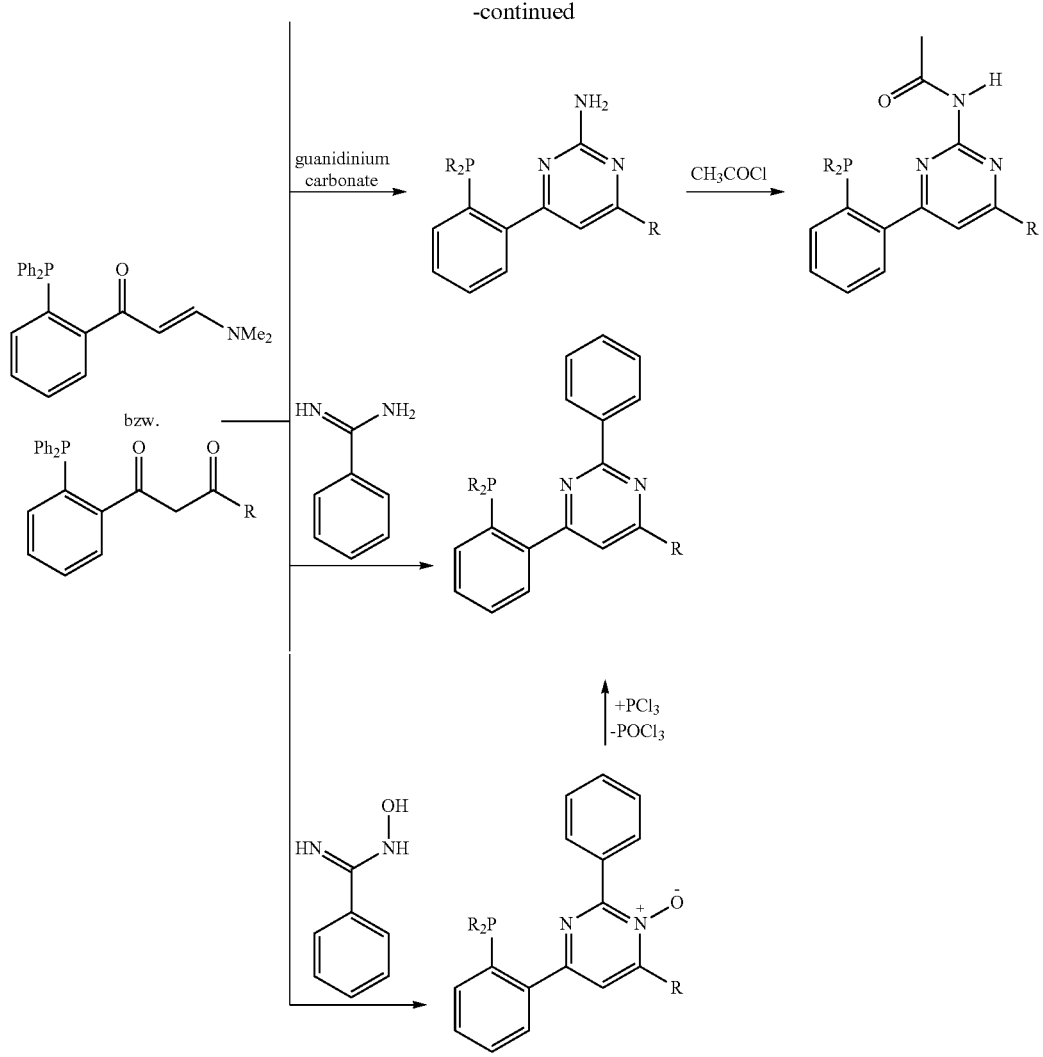

We claim:

1. A method for the manufacture of substituted phosphanes, phosphane oxides, phosphane sulfides, or phosphane selenides corresponding to one of the formulae $P(R_x)(Ar_{3-x})$ or $EP(R_x)(Ar_{3-x})$ or $P(R)(R')(Ar)$ or $EP(R)(R')(Ar)$, wherein x equals 0, 1 or 2;

E corresponds to oxygen, sulfur or selenium;

R and R' are selected from the group consisting of:
- an aryl group (phenyl, polycondensed aromatic group, heterocyclic aromatic group, substituted phenyl group, substituted polycondensed aromatic group, or substituted heterocyclic aromatic group),
- an olefinic group (open-chain or cyclic, with or without functional groups), or
- an alkyl group (open-chain or cyclic, with or without functional groups);

Ar corresponds to an aryl group substituted in ortho, meta, or para position, wherein the same or different aryl groups can be arranged in combination in one compound, with the following substituents:

3(5)-pyrazolyl group, 3-pyrazolyl group substituted in position 1, 3(5)-pyrazolyl group substituted in position 4 and/or 5,3-pyrazolyl group substituted in position 4 and/or 5 as well as in position 1,3-pyrazolyl group substituted in position 4 and/or 5 as well as in position 2, also N-oxide, 1,2-substituted 3-pyrazolium group, 1,2-substituted 3-pyrazolium group substituted in position 4 and/or 5, also N-oxide, each with different anions, 4-pyrimidinyl group, pyrimidine group substituted in position 2 and/or 5 and/or 6, also N-oxide or N,N'-dioxide, wherein the 4-(2-diphenylphosphino-1-naphthyl)-2-R-chinazolines (with R=H, methyl, phenyl, benzyl, i-propyl, t-butyl) and the P-oxides of these compounds are excluded, 4-pyrimidinium group substituted in position 1 or 3, also N-oxide or N,N'-dioxide, or position 2 and/or 5 and/or 6 and in position 1 or 3 substituted 4-pyrimidinium group, also N-oxide or N,N'-dioxide, each with different anions, 4-pyrimidinium group substituted in position 1 and 3, dication, also N-oxide or N,N'-dioxide, 4-pyrimidinium group substituted in position 2 and/or 5 and/or 6 and in position 1 and 3, dication, also N-oxide or N,N'-dioxide, each with different anions;

a 1-oxa-3-di(alkyl or aryl)aminoprop-2-enyl group, 1-oxa-3-di(alkyl or aryl)aminoprop-2-enyl group substituted in 2 and/or 3 position, and;

a 1,3-dioxapropyl group, a 1,3-dioxapropyl group substituted in 2 and/or 3 position, wherein the phosphane oxides and phosphane sulfides of these compounds, in which the carbon atom of the 1-carbonyl group is substituted with a 1-hydroxy-3-oxocyclohex-1-en-2-yl group, are excluded, wherein in selenide compounds, the following anions can occur: $F^{-1}$, $Cl^{-1}$, $B^{-1}$, $I^{-1}$, $OH^{-1}$, $SO_4^{-2}$, $HSO_4^{-1}$, $H_xPO_4^{-1(3-x)}$ (with x=0, 1 or 2), $CO_3^{-2}$ or $HCO_3^{-1}$;

the method is comprising introducing pyrazol or pyrimidine groups, respectively, on aromatic groups for the phosphanes, phosphane oxides, phosphane sulfides or phosphane selenides, step-by-step, starting from acetyl groups, according to the following sequence:

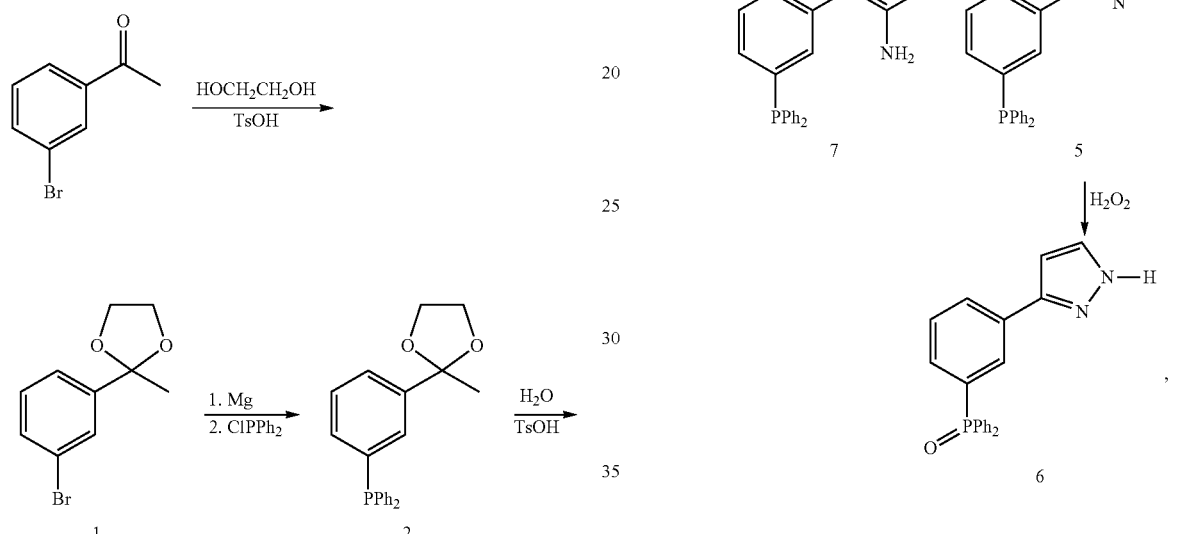

wherein R is as defined above.

* * * * *